United States Patent [19]

Drabb, Jr.

[11] 4,152,436

[45] May 1, 1979

[54] ACYLATED PENTADIENONE HYDRAZONE, METHOD FOR PREPARING THE SAME, AND USE AS FIRE ANT CONTROL AGENTS

[75] Inventor: Thomas W. Drabb, Jr., Trenton, N.J.

[73] Assignee: American Cyanamid Company, Stamford, Conn.

[21] Appl. No.: 934,433

[22] Filed: Aug. 17, 1978

[51] Int. Cl.² .................. C07D 233/52; C07D 237/04
[52] U.S. Cl. .................................... 424/251; 424/244; 424/273 R; 542/417
[58] Field of Search ................ 542/417; 424/244, 251, 424/273 R

[56] References Cited

U.S. PATENT DOCUMENTS

| | | | |
|---|---|---|---|
| 3,878,201 | 4/1975 | Tomcufcik | 542/417 |
| 3,931,152 | 1/1976 | Tomcufcik et al. | 542/417 |
| 4,087,525 | 5/1978 | Lovell | 424/244 |

*Primary Examiner*—Arthur P. Demers
*Attorney, Agent, or Firm*—Harry H. Kline

[57] ABSTRACT

There are provided certain acylated pentadienone hydrazones, and methods of use of said compounds for the control of insects, especially Lepidopterous insects, and for the control of ants, Family Formicidae, especially fire ants.

26 Claims, No Drawings

ACYLATED PENTADIENONE HYDRAZONE, METHOD FOR PREPARING THE SAME, AND USE AS FIRE ANT CONTROL AGENTS

The present invention relates to insecticidal acylated pentadienone hydrazones of formula (I):

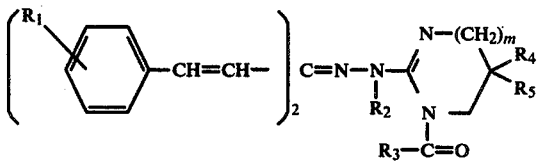

wherein $R_1$ is in the meta or para position and is selected from the group consisting of halogen, $CF_3$—, $CHF_2CF_2O$— or $CH_nF_{3-n}Y$—; $R_2$ is hydrogen or

$R_3$ and $R_6$ may be the same or different and are selected from $C_1$–$C_{17}$ alkyl, $C_2$–$C_{17}$ alkenyl or

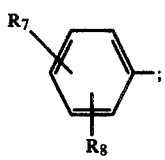

$R_4$ and $R_5$ are each hydrogen or methyl; $R_7$ and $R_8$ are hydrogen, halogen, $C_1$–$C_4$ alkyl or $C_1$–$C_4$ alkoxy; Y is oxygen or sulfur; m is an integer selected from 0, 1 or 2; n is an integer selected from 0 or 1.

A preferred group of compounds represented by formula (I) are those wherein $R_1$ is p-trifluoromethyl; $R_2$ is hydrogen or

$R_3$ and $R_6$ may be the same or different and are selected from $C_1$–$C_{17}$ alkyl, $C_2$–$C_{17}$ alkenyl or

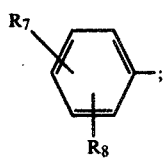

$R_7$ and $R_8$ are selected from hydrogen, halogen, $C_1$–$C_4$ alkyl or $C_1$–$C_4$ alkoxy; and m is 0 or 1.

Another preferred group of compounds represented by formula (I) are those wherein $R_1$ is p-trifluoromethyl; $R_2$ is hydrogen or

$R_3$ and $R_6$ are the same, and are selected from $C_1$–$C_{17}$ alkyl, $C_2$–$C_{17}$ alkenyl or

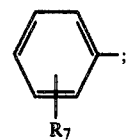

$R_4$ and $R_5$ are methyl; $R_7$ is hydrogen, halogen or $C_1$–$C_4$ alkyl and m is 1.

In general, the compounds of formula (I) wherein $R_2$ is hydrogen, can be conveniently prepared by acylating a pentadienone hydrazone with an acid halide as shown below:

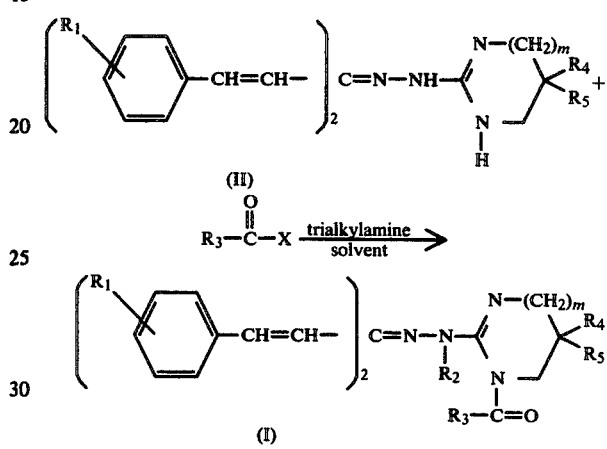

wherein each of the R groups and m are as hereinabove defined; X is halogen, preferably chlorine.

Accordingly, a pentadienone hydrazone of formula (II) is reacted with an equimolar or even a slight excess of an acid halide, preferably chloride, of formula:

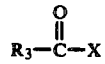

in the presence of an inert solvent such as benzene, toluene, xylene, dioxane, tetrahydrofuran, ether and the like and a ($C_1$–$C_5$) trialkylamine at a temperature of 10° to 30° C. for a period of time sufficient to complete the reaction. When two or more moles of acid halide are employed in the above reaction, formula (I) compounds are obtained wherein $R_2$ is

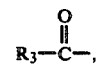

and where each of the Rs are as above-defined. Alternatively, the now-acylated compound of structure (I) wherein $R_2$ is H may be acylated a second time with a different acylating agent

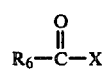

to give formula (I) products in which $R_2$ is

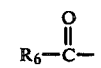

and where each of the R's are as above-defined. The thus-obtained compounds of formula (I) may be purified, if desired, by procedures such as recrystallization, column chromatoraphy and the like.

Advantageously, the acylated pentadienone hydrazones of the present invention are three to twenty times more soluble in solvents and vegetable oils, than are their immediate corresponding precursors. The increased solubility of formula (I) compounds is of advantage in the preparation of various liquid concentrates and of baits.

In general, the formula (II) compounds, can be conveniently prepared by a reaction sequence graphically illustrated as follows:

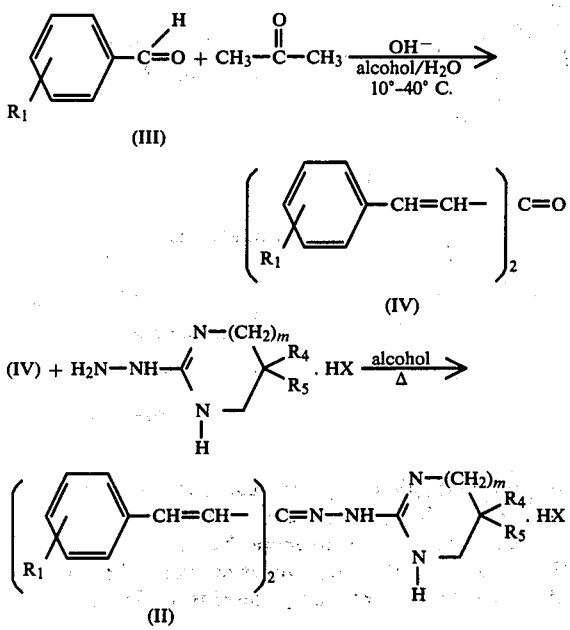

wherein each of the R groups and m are as hereinabove defined and HX represents a mono or divalent inorganic acid. In the above sequence, the product (II) is shown as the HX salt. The corresponding pentadienone hydrazone free base can be obtained further by treating same with an aqueous solution of a base, such as sodium or potassium bicarbonate, sodium or potassium carbonate, sodium or potassium hydroxide, ammonium hydroxide or triethylamine.

It is a good practice to react two moles of an aldehyde of formula (III) above with one mole of acetone in an aqueous alcohol in the presence of an alkali metal base, such as sodium or potassium hydroxide at a temperature range of 10° C. to 40° C., preferably at from 20° C. to 25° C., for a period of time ranging from one to three hours, or until the condensation reaction is essentially complete to afford the corresponding pentadienone (IV). Next, the thus-obtained pentadienone is condensed with an equimolar (or even a slight excess) amount of a salt of the appropriate hydrazine (V) in an alcohol at 50° C. to 80° C. or at the boiling point of said alcohol for a period of time of one to five hours or until the condensation reaction is essentially complete to yield the salt of a formula (II) pentadienone hydrazone. The alcohols used in the above reaction sequences are illustratively methanol, ethanol, isopropanol, and mixtures thereof. The pentadienone hydrazone may be recovered from the above salt, if desired, by treating said salt with a dilute aqueous solution of an inorganic base, such as sodium or potassium bicarbonate, sodium or potassium carbonate, sodium or potassium hydroxide, ammonium hydroxide or triethylamine.

The compounds of the present invention find utility in the control of insects and ants, Family Formicidae, by contacting said insects with, and/or applying to their habitat or food supply, an insecticidally effective amount of a compound of formula (I):

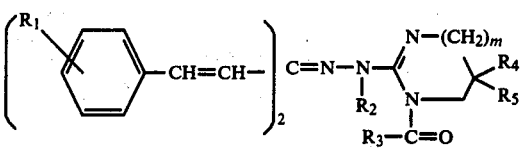

wherein $R_1$ to $R_5$ and m are as hereinabove defined. Further, the compounds find utility in protecting agronomic crops, trees, shrubs, ornamentals and the like from attack by insects, by applying to the crops an insecticidally effective amount of a compound having the above structure. In practice, generally about 0.14 kg/hectare to 11.2 kg/hectare, and preferably 0.56 kg/hectare to 4.48 kg/hectare of a formula (I) acylated pentadienone hydrazone is effective for insect control other than through the use of baits as disclosed below and/or for crop protection.

The formula (I) compounds of this invention can be applied in either liquid or solid form. They may be applied in solid form as dusts or dust concentrates, or in liquid form as emulsifiable concentrates, flowable (thixotropic) formulations or wettable powders which are dispersed in water or other inexpensive liquid for application as a finely divided spray.

The formula (I) compounds may also be prepared in the form of an attractant bait which is distributed in the locus or habitat of the insects sought to be controlled.

A typical emulsifiable concentrate can be prepared by admixing from about 12% to 29% by weight of acylated pentadienone hydrazone, about 8% to 12% by weight of a blend on nonionic emulsifiers such as TMulz 339 (sold by Thompson-Hayward of Kansas City, Kan.), or polyoxyethylene derivatives and blends with alkyl aryl sulfonates, and about 59% to 80% by weight of cyclohexanone or a heavy aromatic solvent having a mixed aniline point between −1° C. and 35.0° C., a specific gravity between 0.880 and 1.5 at 15.5°/15.5° C. and an aromatic content of 60% to 100%. These formulations provide from 119.8 g/liter to 239.6 g/liter of active compound and are generally diluted with water for application as a dilute liquid. However, said formulations can also be applied in the form of undiluted discrete droplets as low volume or ultra-low volume sprays. For such application, the emulsifiable concentrate is usually applied with apparatus designed to disperse the liquid in the form of finely divided discrete droplets having a mass median diameter of from 25 to 150 microns.

A typical wettable powder formulation can be prepared by grinding together about 34% by weight of a synthetic calcium silicate, 12% by weight of a dispersing agent such as sodium lignosulfonate, 4% by weight of a wetting agent such as an alkyl aryl sulfonate, and 50% by weight of acylated pentadienone hydrazone. Such formulation is generally dispersed in water for application as a liquid spray.

We have found that acylated pentadienone hydrazones, as represented by the formula set forth above, are useful for the control of insects, especially a wide variety of Lepidopterous insects.

The compounds of this invention are active against Lepidopterous larvae such as southern armyworms [*Spodoptera eridania* (Cramer)], cabbage loopers [*Trichoplusia ni* (Hübner)], tobacco budworms [*Heliothis virescens* (Fabricius)], and the like, at 10 to 1000 ppm rates. They do not appear to be especially toxic to most beneficial insects and thus are useful for pest management and integrated control programs. Moreover, these compounds show virtually no phytotoxicity to plants at rates of application up to 11.2 kg/hectare.

Advantageously, the formula (I) acylated pentadienone hydrazone compounds of the present invention are active as stomach poisons. Thus, they are effective against insects with chewing mouth parts (Orthopterous insects such as cockroaches, grasshoppers, crickets and Isopterous insects such as termites) as well as those with sponge and lapping mouth parts (Dipterous insects such as flies). They are effective for the control of fire ants, such as the southern fire ant, *Solenopsis xyloni*, the black imported fire ant, *Solenopsis richteri*, and the red imported fire ant, *Solenopsis invicta*. They are also effective for the control of ants such as the big-headed ant, *Pheidole megacephala*, and the Argentine ant, *Iridomyrmax humilis*, that are dominant pests in pineapple and sugarcane fields, and for the control of many species of ants that are classified under the general category of household ants. Ants are serious economic and public health pests. Serious problems created by fire ants include stinging of humans and livestock, feeding on plants, particularly on seedlings and on germinating seeds, damage to farm machinery that strike ant mounds, loss of crops and refusal of workers to enter infested fields to cultivate and harvest crops. Ants invade houses, crawl over food, carry bits of food to their nests and also cause damage by establishing their nests in the woodwork of houses and other wooden buildings.

Control of these pests can be achieved with treated baits that are distributed in or adjacent to the infested area, such as pasture, park dwellings or other locations in which ant control is desired, and made available to worker ants. The workers carry the treated bait to the colony where it is consumed by the queens and the young ants, leading to their destruction.

In practice, generally from about 1.25 g/ha to 75.0 g/ha, and preferably from 2.5 g/ha to 37.5 g/ha, of the acylated pentadienone hydrazone is effective for fire ant control and/or for crop protection from ants and about 0.0625% to 4% by weight, and preferably 0.125% to 2.0% by weight of the acylated pentadienone hydrazone is effective for the control of house ants and/or insects that are controlled by bait.

Baits can be prepared, for example, by admixing said formula (I) compounds with peanut butter or citrus pulp, vegetable oils such as soybean oil, animal fats such as lard and tallow, and with or without an organic filler such as bran, and/or an attractant such as lecithin. The composition is then placed in soda straws or on a carrier such as puffed grain, corncob grits and/or starch matrix and distributed in the area of the colony or infestation. Use of these baits has particular advantage, since such method of distribution poses little or no hazard to non-target organisms that may frequent the infested area.

The invention is further illustrated by the examples set forth below which are provided only by way of illustration and are not deemed to be limiting thereof. Unless otherwise noted, all parts are by weight.

EXAMPLE 1

Preparation of 1,5-bis($\alpha,\alpha,\alpha$-Trifluoro-p-tolyl)-1,4 pentadien-3-one (1,4,5,6-tetrahydro-5,5-dimethyl-2-pyrimidinyl)hydrazone.

To a mixture of 2.1 g of 5,5-dimethyl-1,4,5,6-tetrahydropyrimidin-2-ylhydrazine hydroiodide and 3.2 g of 1,5-bis($\alpha,\alpha,\alpha$-trifluoro-p-tolyl)-1,4-pentadiene-3-one in 6 ml of absolute ethanol was added one drop of 47% hydriodic acid. The mixture was heated at reflux for 2 to 3 hours and then cooled in ice. The yellow hydroiodide salt which precipitated was collected by filtration and washed with ethanol.

The hydroiodide salt was neutralized by stirring with 15 ml of ethyl acetate and 15 ml of saturated sodium carbonate solution. The ethyl acetate mixture was separated from the aquoeus phase, dried over magnesium sulfate, and concentrated to give a red oil. The oil was mixed with a little ether, and the mixture refrigerated. The resulting solids were collected and washed with ether and amounted to 1.2 g, melting point 163.5°–164.5° C.

Analysis calculated for $C_{25}H_{24}F_6N_4$: C, 60.72; H, 4.89; N, 11.33; Found: C, 60.54; H, 4.73; N, 10.43.

The product exists in different crystalline forms, and when recrystallized from isopropyl alcohol, has a melting point of 189°–191° C.

By the above procedure but substituting the appropriate hydrazines and pentadienones, the following compounds are prepared:

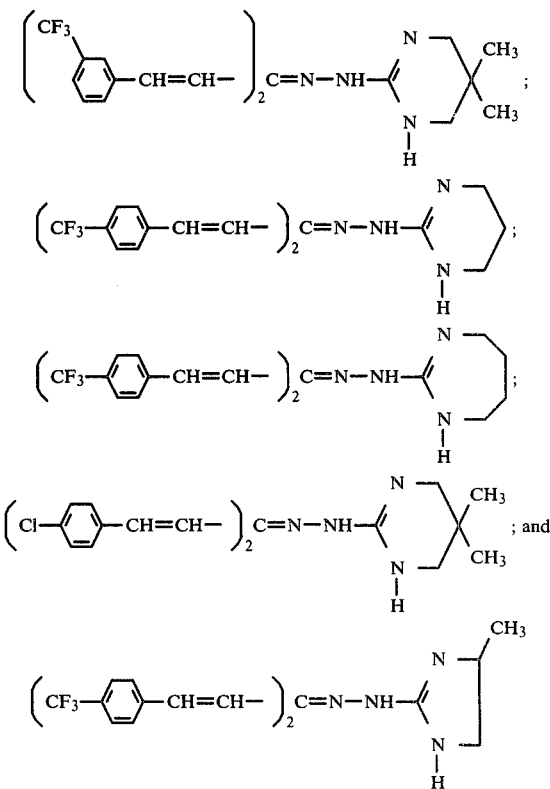

EXAMPLE 2

Preparation of 1,5-bis(α,α,α-Trifluoro-p-tolyl)-1,4-pentadien-3-one, (1-acetyl-1,4,5,6-tetrahydro-5,5-dimethyl-2-pyrimidinyl)hydrazone.

A solution of acetyl chloride (0.785 g; 0.01 mole) in ether (10 ml) is added dropwise to a stirred suspension of 1,5-bis(α,α,α-trifluoro-p-tolyl)-1,4-pentadien-3-one, (1,4,5,6-tetrahydro-5,5-dimethyl-2-pyrimidinyl)hydrazone (4.95 g; 0.01 mole) in ether (50–100 ml) and triethylamine (1.01 g; 0.01 mole). The reaction mixture is stirred for several hours and is then filtered. The solids are washed with ether, the wasings and the filtrate are combined and evaporated to yield 4.2 g of a bright yellow solid (78%). The solid is recrystallized from isopropanol to afford the title product, m.p. 171°–173° C.

Analysis calculated for $C_{27}H_{26}F_6N_4O$: C, 60.46; H, 4.85; N, 10.45; Found: C, 60.10; H, 4.81; N, 10.55.

EXAMPLE 3

Preparation of acylated pentadienone hydrazones

By the method of Example 1, but substituting various acid chlorides and hydrazones in the reaction, a number of acylated pentadienone hydrazones are prepared.

The compounds thus prepared are listed in Table I below.

TABLE I

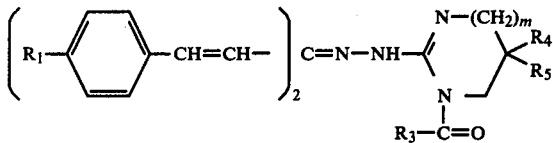

| $R_1$ | $R_3$ | $R_4$ | $R_5$ | m | m.p. °C. |
|---|---|---|---|---|---|
| $CF_3-$ | phenyl | $CH_3-$ | $CH_3-$ | 1 | 153–155 |
| $CF_3-$ | $n-C_{15}H_{31}-$ | $CH_3-$ | $CH_3-$ | 1 | 102.5–104.0 |
| $CF_3-$ | $Cl-C_6H_4-$ | $CH_3-$ | $CH_3-$ | 1 | 157–158.8 |
| $CF_3-$ | $CH_3-$ | $H-$ | $H-$ | 2 | 153–157 |
| $CF_3-$ | $(CH_3)_2CH-$ | $CH_3-$ | $CH_3-$ | 1 | 192–194 |
| $CF_3-$ | $n-C_7H_{15}-$ | $CH_3-$ | $CH_3-$ | 1 | 128–130 |
| $CF_3-$ | phenyl | $H-$ | $H-$ | 2 | 219–220.5 |
| $CF_3-$ | $n-C_7H_{15}-$ | $H-$ | $H-$ | 2 | 92.5–97.0 |
| $CF_3-$ | $n-C_5H_{11}-$ | $CH_3-$ | $CH_3-$ | 1 | 153–155 |
| $CF_3-$ | $n-C_{11}H_{23}-$ | $CH_3-$ | $CH_3-$ | 1 | 110–112.5 |
| $CF_3-$ | $n-C_{13}H_{27}-$ | $CH_3-$ | $CH_3-$ | 1 | 107–108 |
| $CF_3-$ | $n-C_9H_{19}-$ | $CH_3-$ | $CH_3-$ | 1 | 124–126 |
| $Cl-$ | $CH_3-$ | $CH_3-$ | $CH_3-$ | 1 | 178–180 |
| $CF_3-$ | $n-C_{15}H_{31}-$ | $H-$ | $H-$ | 2 | 57.5–61.5 |
| $CF_3-$ | $CH_3(CH_2)_3\text{-}CH\text{-}C_2H_5$ | $CH_3-$ | $CH_3-$ | 1 | 107–108.5 |
| $CF_3-$ | phenyl-CH=CH- | $CH_3-$ | $CH_3-$ | 1 | 155–158 |
| $CF_3-$ | $(CH_3)_3C$-phenyl | $CH_3-$ | $CH_3-$ | 1 | 110 (dec) |
| $CF_3-$ | $n-C_8H_{17}-CH=CH-(CH_2)_7-$ | $CH_3-$ | $CH_3-$ | 1 | thick gum |
| $CF_3-$ | $n-C_4H_9-$ | $CH_3-$ | $CH_3-$ | 1 | 151–156 |
| $Cl-$ | phenyl | $CH_3-$ | $CH_3-$ | 1 | 191–193 |
| $CF_3-$ | $(CH_3)_2C=CH-$ | $CH_3-$ | $CH_3-$ | 1 | 143–147 |
| $CF_3-$ | $CH_3-$ | $H-$ | $H-$ | 1 | 170–172 |
| $Cl$ | $n-C_{15}H_{31}-$ | $CH_3-$ | $CH_3-$ | 1 | 105–107 |
| $CF_3-$ | $CH_3-$ | $CH_3-$ | $H-$ | 0 | — |
| $CF_3-$ | $n-C_5H_{11}-$ | $CH_3-$ | $H-$ | 0 | — |
| $CF_3O-$ | $CH_3-$ | $CH_3-$ | $CH_3-$ | 1 | — |
| $CHF_2O-$ | $C_2H_5-$ | $H-$ | $H-$ | 2 | — |
| $CF_3S-$ | $CH_3CH_2-CH_2-$ | $CH_3-$ | $CH_3-$ | 1 | — |

TABLE I-continued

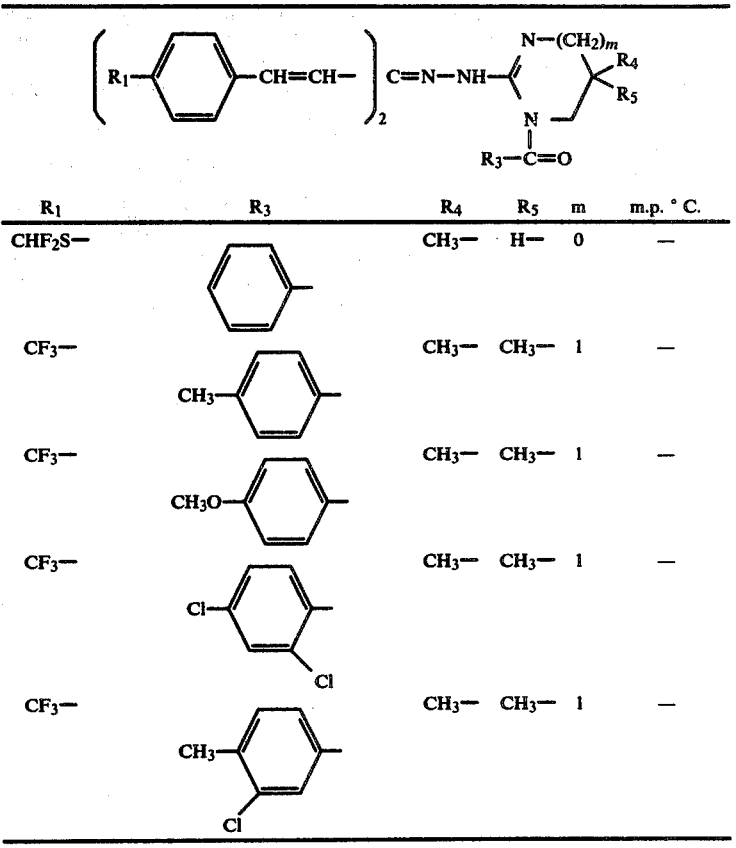

| R₁ | R₃ | R₄ | R₅ | m | m.p. °C. |
|---|---|---|---|---|---|
| CHF₂S— | phenyl | CH₃— | H— | 0 | — |
| CF₃— | 4-methylphenyl | CH₃— | CH₃— | 1 | — |
| CF₃— | 4-methoxyphenyl | CH₃— | CH₃— | 1 | — |
| CF₃— | 2,4-dichlorophenyl | CH₃— | CH₃— | 1 | — |
| CF₃— | 2-chloro-4-methylphenyl | CH₃— | CH₃— | 1 | — |

EXAMPLE 4

Preparation of Acetic Acid, (1-acetyl-1,4,5,6-tetrahydro-5,5-dimethyl-2-pyrimidinyl){p-(trifluoromethyl)-α-[p-(trifluoromethyl)styryl]cinnamylidene}hydrazide A solution of acetyl chloride (1.57 g; 0.02 mole) in ether (10 ml) is added dropwise to a stirred suspension of 1,5-bis(α,α,α-trifluoro-p-tolyl)-1,4-pentadien-3-one, (1,4,5,6-tetrahydro-5,5-dimethyl-2-pyrimidinyl)hydrazone (4.95 g; 0.01 mole) in ether (50–100 ml) and triethylamine (2.02 g; 0.02 mole). The reaction mixture is then stirred for several hours and is filtered. The solids are washed with ether, the washings and filtrate are combined and concentrated in vacuo to yield 5.4 g (93%) of a yellow colored glass. The sample is recrystallized from toluene and hexane, m.p. 70°–72° C.

Analysis calculated for $C_{29}H_{28}F_6N_4O_2$: C, 60.72; H, 4.84; N, 9.69; Found: C, 60.32; H, 5.06; N, 9.70.

By the above procedure, but substituting various acid chlorides and hydrazones in the reaction, the following bis-acylated pentadienone hydrazones can be prepared:

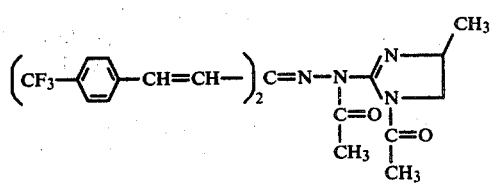

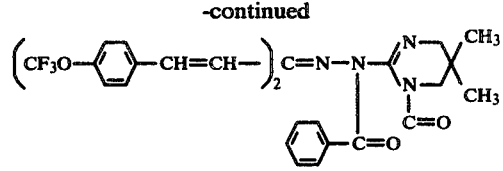

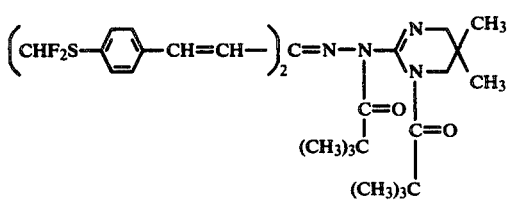

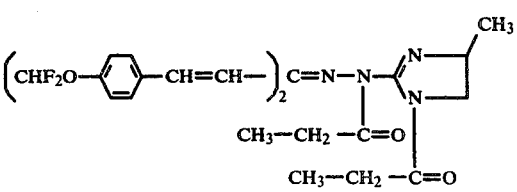

EXAMPLE 5

Preparation of Benzoic Acid, (1-acetyl-1,4,5,6-tetrahydro-5,5-dimethyl-2-pyrimidinyl)}p-(trifluoromethyl)-α-[p-(trifluoromethyl)styryl]cinnamylidene}hydrazide The product of Example 2 is acylated with benzoyl chloride by the method of Example 2 to afford the title compound, a yellow solid.

EXAMPLE 6

Determination of the Solubility of the Compounds of the Invention in Soybean Oil

Method

From a pre-weighed sample of the compound under test, small amounts are added periodically to a stirred sample of soybean oil (1.0 g) until the last small amount added does not dissolve completely. The sample of the compound is then reweighed, the difference between the initial and final weights corresponding to the weight of the compound in solution. The solubility data thus obtained are summarized in Table II below.

TABLE II

Solubility of compounds of the invention in soybean oil.

| Compound | Solubility in Soybean oil In g/g of oil | In % of w/w |
|---|---|---|
| $\left(CF_3-\bigcirc-CH=CH-\right)_2 C=N-NH-\underset{H}{\overset{N}{\underset{N}{\bigcirc}}}\underset{CH_3}{\overset{CH_3}{\bigcirc}}$ (* unacylated starting material) | 0.001 | 0.1 |
| $\left(CF_3-\bigcirc-CH=CH-\right)_2 C=N-NH-\underset{CH_3-C=O}{\overset{N}{\underset{N}{\bigcirc}}}\underset{CH_3}{\overset{CH_3}{\bigcirc}}$ | 0.003 | 0.3 |
| $\left(CF_3-\bigcirc-CH=CH-\right)_2 C=N-NH-\underset{\phi-C=O}{\overset{N}{\underset{N}{\bigcirc}}}\underset{CH_3}{\overset{CH_3}{\bigcirc}}$ | 0.004 | 0.4 |
| $\left(CF_3-\bigcirc-CH=CH-\right)_2 C=N-NH-\underset{n-C_{15}H_{31}-C=O}{\overset{N}{\underset{N}{\bigcirc}}}\underset{CH_3}{\overset{CH_3}{\bigcirc}}$ | 0.02 | 2.0 |

\* = unacylated starting material.

EXAMPLE 7

Insecticide Testing Procedures

Tobacco Budworm [*Heliothis virescens* (Fabricius)]

A cotton plant with 2 true leaves expanded is dipped for 3 seconds with agitation in a 300 ppm solution. A 1.25 to 2 cm square of cheesecloth with about 50 to 100 budworm eggs 0–24 hours old is also dipped in the test solution and placed on one leaf to dry. The leaf with the treated budworm eggs is removed from the plant and placed in a 236.6 ml (8-oz) Dixie cup with a wet 5 cm piece of dental wick and covered with a lid. The other leaf is placed in a similar cup with a wick and a piece of cheesecloth infested with 50–100 newly hatched larvae is added before covering the cup with a lid. After 3 days at 26.7° C., observations of egg hatch are made as well as kill of newly hatched larvae, any inhibition of feeding, or interference of any sort with normal development.

Third Instar

Three cotton plants with just expanded cotyledons are dipped in a 1000 ppm solution, and placed in a hood to dry. When dry, each cotyledon is cut in half and each half is placed in one of ten 29.6 ml plastic medicine cups containing a 1.25 cm dental wick saturated with water, and one third instar budworm larva is added. The cup is capped and held for 3 days at 26.7° C., after which mortality counts are made.

Southern Armyworm [*Spodoptera eridania* (Cramer)]

A Sieva lima bean plant with just the primary leaves expanded to 7.6 to 10 cm is dipped for 3 seconds with agitation in a 1000 ppm solution and set in a hood to dry. Following this, one leaf is placed in a 10 cm petri dish which has a moist filter paper in the bottom and 10 thrid instar armyworm larvae about 1 cm long. The dish is covered and held at 26.7° C. After 2 days mortality counts and estimates of the amount of feeding are made. Compounds showing partial kill and/or inhibition of feeding are held for an extra day for further observations.

All compounds showing activity as defined above are retested, using the second leaf on the bean plant, after an interval of 7 days from original treatment, as an assay of residual activity.

Cabbage Looper [*Trichoplusia ni* (Hubner)]

A primary leaf of a cotton plant is dipped in the test solution and agitated for 3 seconds. It is then set in a hood to dry. Following this, the leaf is placed in a 10 cm petri dish containing a moist filter paper at the bottom and 10 third-instar loopers. The dish is covered and held at 26.7° C. After 2 days, mortality counts and estimates of feeding damage are recorded. Those materials showing partial kill and/or inhibition of feeding are held for another day for further observations.

The rating system employed in these tests is as follows:

Rating System

0 = 0-40% killed or affected
1 = reduced feeding (trace to light damage)
2 = some deformed insects (40-80%)
3 = mostly deformed insects (85-100%)
4 = not an index number at present
5 = 41-60% mortality
6 = 61-70% mortality
7 = 71-85% mortality
8 = 86-95% mortality
9 = 100% mortality The absence of a number indicates that no test has been run at that particular dosage.

Compounds rated active (8 or 9) are further tested at reduced concentrations in 50% acetone:50% water.

Data obtained are reported in Tables (IIIa) and (IIIb) below.

TABLE (IIIa)

Efficacy of the compounds of the invention for the control of Lepidopterous Insects, expressed as % kill per ppm of compound.

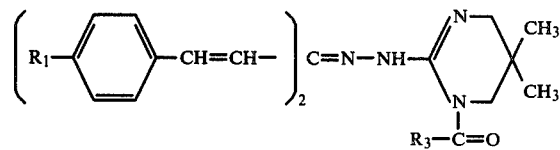

| | | Tobacco Budworm | | | | | | Southern Armyworm | | | | Cabbage Looper | | |
|---|---|---|---|---|---|---|---|---|---|---|---|---|---|---|
| | | 1st Instar | | | 3rd Instar | | | 3rd Instar | | | | 3rd Instar | | |
| $R_1$ | $R_3$ | 300 ppm | 100 ppm | 10 ppm | 1000 ppm | 100 ppm | 10 ppm | 1000 ppm | 100 ppm | 10 ppm | 7 days | 1000 ppm | 100 ppm | 10 ppm |
| $CF_3-$ | $CH_3-$ | 86-95 | 0-40 | | 100 | 100 | 40 | 100 | 100 | 0 | 100 | 100 | 86-95 | 41-60 |
| $CF_3-$ | $(CH_3)_2CH-$ | 86-95 | | | 100 | 50 | 0 | 100 | 100 | 0 | | 100 | 100 | 0 |
| $CF_3-$ | $n-C_4H_9-$ | 86-95 | | | 100 | 40 | | 100 | 100 | 0 | 100 | 100 | 100 | |
| $CF_3-$ | $(CH_3)_2C=CH-$ | 0 | | | 100 | 0 | | 100 | 0 | | 0 | 100 | 10 | |
| $CF_3-$ | $n-C_5H_{11}-$ | 0 | | | 100 | 70 | 0 | 100 | 100 | 0 | | 100 | 50 | 0 |
| $CF_3-$ | phenyl | 100 | 0-40 | | 100 | 100 | 0 | 100 | 100 | 0 | 100 | 100 | 100 | 0 |
| $CF_3-$ | Cl-phenyl | 0 | | | 100 | 60 | 0 | 100 | 100 | 0 | 0 | 100 | 70 | 0 |
| $CF_3-$ | $n-C_7H_{15}-$ | 0 | | | 100 | 0 | | 100 | 90 | 0 | | 100 | 90 | |
| $CF_3-$ | $CH_3(CH_2)_3$-CH($C_2H_5$)- | 0 | | | 100 | 40 | | 100 | 100 | 0 | | 100 | 90 | 80 |
| $CF_3-$ | phenyl-CH=CH- | 0 | | | — | | | 0 | | | | — | | |
| $CF_3-$ | $n-C_9H_{19}-$ | 0 | | | 100 | 100 | 0 | 100 | 0 | | | 100 | 60 | 0 |
| $CF_3-$ | $(CH_3)_3C$-phenyl | 86-95 | 0-40 | 0-40 | 100 | 100 | 0 | 100 | 90 | 0 | 0 | 100 | 100 | 0 |
| $CF_3-$ | $n-C_{11}H_{23}-$ | 0 | | | 100 | 70 | 0 | 100 | 100 | 0 | | 100 | 70 | 0 |
| $CF_3-$ | $n-C_{13}H_{27}-$ | 0 | | | 100 | 90 | 0 | 100 | 0 | | | 100 | 60 | 0 |
| $CF_3-$ | $n-C_{15}H_{31}-$ | 86-95 | 0-40 | | 100 | 30 | 0 | 100 | 100 | 0 | 80 | 100 | 60 | 0 |
| $CF_3-$ | $n-C_8H_{17}-CH=CH-(CH_2)_7-$ | 100 | 100 | 0-40 | 100 | 100 | 0 | 100 | 100 | 20 | 100 | 100 | 100 | 0 |
| $Cl-$ | $CH_3-$ | 100 | 100 | 0-40 | 100 | 100 | 0 | 100 | 100 | | | 100 | 100 | 0 |
| $Cl-$ | phenyl | 100 | 41-60 | 0-40 | 100 | 0 | | 100 | 100 | 30 | 100 | 100 | 100 | 0 |
| $Cl-$ | $n-C_{15}H_{31}-$ | 0 | | | 100 | 0 | | 100 | 0 | | 100 | 100 | 0 | |

TABLE (IIIb)

Efficacy of the compounds of the invention for the control of Lepidopterous Insects, expressed as % kill per ppm of compound.

| Compound | Tobacco Budworm 1st Instar | | | Tobacco Budworm 3rd Instar | | Southern Armyworm 3rd Instar | | | Cabbage Looper 3rd Instar | | |
|---|---|---|---|---|---|---|---|---|---|---|---|
| | 300 ppm | 100 ppm | 10 ppm | 1000 ppm | 100 ppm | 1000 ppm | 100 ppm | 10 ppm | 7 days | 1000 ppm | 100 ppm | 10 ppm |
| $\left[ CF_3-\bigcirc-CH=CH-C=N-NH- \right]_2 \; C_6H_5-C=O$ | 0-40 | | | — | | — | | | | — | | |
| $\left[ CF_3-\bigcirc-CH=CH-C=N-NH- \right]_2 \; n\text{-}C_7H_{15}-C=O$ | 0-40 | | | — | | — | | | | — | | |
| $\left[ CF_3-\bigcirc-CH=CH-C=N-NH- \right]_2 \; n\text{-}C_{15}H_{31}-C=O$ | 0-40 | 41-60 | 0-40 | 100 | 70 | 100 | 100 | 0 | 100 | 100 | 100 | 0 |
| $\left[ CF_3-\bigcirc-CH=CH-C=N-NH- \right]_2 \; CH_3-C=O$ | 100 | 100 | 0 | 100 | 0 | 100 | 0 | 0 | 0 | 100 | 100 | 0 |
| Compound of Example 4 | 100 | | | 100 | | 100 | | | | 100 | 86-95 | 41-60 |

We claim:
1. A compound having the structure:

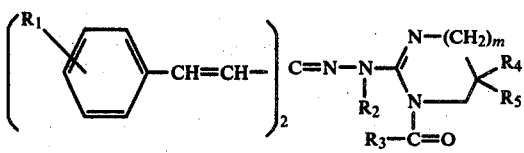

wherein $R_1$ is in the meta or para position and is selected from the group consisting of halogen, $CF_3$—, $CHF_2CF_2O$— or $CH_nF_{3-n}Y$—; $R_2$ is hydrogen or

$R_3$ and $R_6$ may be the same or different and are selected from $C_1$-$C_{17}$ alkyl, $C_2$-$C_{17}$ alkenyl or

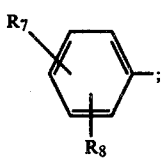

$R_4$ and $R_5$ are each hydrogen or methyl; $R_7$ and $R_8$ are hydrogen, halogen, $C_1$-$C_4$ alkyl or $C_1$-$C_4$ alkoxy; Y is oxygen or sulfur; m is an integer selected from 0, 1 or 2; n is an integer selected from 0 or 1.

2. A compound according to claim 1, wherein $R_1$ is p-trifluoromethyl; $R_2$ is hydrogen or

$R_3$ and $R_6$ may be the same or different and are selected from $C_1$-$C_{17}$ alkyl, $C_2$-$C_{17}$ alkenyl or

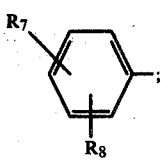

$R_7$ and $R_8$ are selected from hydrogen, halogen, $C_1$-$C_4$ alkyl or $C_1$-$C_4$ alkoxy; and m is 0 or 1.

3. A compound according to claim 1, wherein $R_1$ is p-trifluoromethyl; $R_2$ is hydrogen or

$R_3$ and $R_6$ are the same, and are selected from $C_1$-$C_{17}$ alkyl, $C_2$-$C_{17}$ alkenyl or

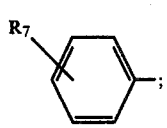

$R_4$ and $R_5$ are methyl; $R_7$ is hydrogen, halogen or $C_1$-$C_4$ alkyl; m is 1.

4. The compound according to claim 1, 1,5-bis-(α,α,α-trifluoro-p-tolyl)-1,4-pentadien-3-one(1-acetyl-1,4,5,6-tetrahydro-5,5-dimethyl-2-pyrimidinyl)hydrazone.

5. The compound according to claim 1, 1,5-bis-(α,α,α-trifluoro-p-tolyl)-1,4-pentadien-3-one(1,4,5,6-tetrahydro-1-isobutyryl-5,5-dimethyl-2-pyrimidinyl)hydrazone.

6. The compound according to claim 1, 1,5-bis-(α,α,α-trifluoro-p-tolyl)-1,4-pentadien-3-one(1,4,5,6-tetrahydro-5,5-dimethyl-1-valeryl-2-pyrimidinyl)hydrazone.

7. The compound according to claim 1, 1,5-bis-(α,α,α-trifluoro-p-tolyl)-1,4-pentadien-3-one[1,4,5,6-tetrahydro-5,5-dimethyl-1-(9-octadecenoyl)-2-pyrimidinyl]hydrazone.

8. The compound according to claim 1, 1,5-bis-(α,α,α-trifluoro-p-tolyl)-1,4-pentadien-3-one(1-benzoyl-1,4,5,6-tetrahydro-5,5-dimethyl-2-pyrimidinyl)hydrazone.

9. The compound according to claim 1, 1,5-bis-(p-chlorophenyl)-1,4-pentadien-3-one(1-acetyl-1,4,5,6-tetrahydro-5,5-dimethyl-2-pyrimidinyl)hydrazone.

10. The compound according to claim 1, 1,5-bis-(p-chlorophenyl)-1,4-pentadien-3-one(1-benzoyl-1,4,5,6-tetrahydro-5,5-dimethyl-2-pyrimidinyl)hydrazone.

11. The compound according to claim 1, 1,5-bis-(α,α,α-trifluoro-p-tolyl)-1,4-pentadien-3-one-(1-acetyl-1,4,5,6-tetrahydro-2-pyrimidinyl)hydrazone.

12. A method for controlling insects comprising contacting said insects, their habitat, and/or their food supply, with an insecticidally effective amount of a compound having the structure:

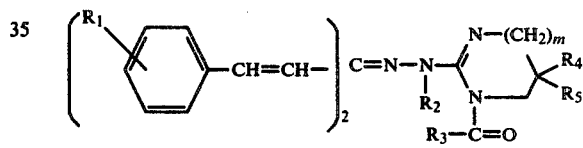

wherein $R_1$ is in the meta or para position and is selected from the group consisting of halogen, $CF_3$—, $CHF_2CF_2O$— or $CH_nF_{3-n}Y$—; $R_2$ is hydrogen or

$R_3$ and $R_6$ may be the same or different and are selected from $C_1$-$C_{17}$ alkyl, $C_2$-$C_{17}$ alkenyl or

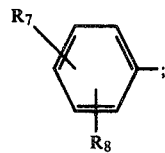

$R_4$ and $R_5$ are each hydrogen or methyl; $R_7$ and $R_8$ are hydrogen, halogen, $C_1$-$C_4$ alkyl or $C_1$-$C_4$ alkoxy; Y is oxygen or sulfur; m is an integer selected from 0, 1 or 2; n is an integer selected from 0 or 1.

13. The method according to claim 12, wherein $R_1$ is p-trifluoromethyl; $R_2$ is hydrogen or $R_6-\overset{O}{\underset{\|}{C}}-$;

$R_3$ and $R_6$ may be the same or different and are selected from $C_1$-$C_{17}$ alkyl, $C_2$-$C_{17}$ alkenyl or

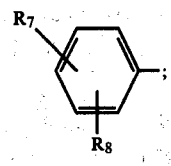

$R_7$ and $R_8$ are selected from hydrogen, halogen, $C_1$-$C_4$ alkyl or $C_1$-$C_4$ alkoxy; and m is 0 or 1.

14. The method according to claim 12, wherein $R_1$ is p-trifluoromethyl; $R_2$ is hydrogen or

$R_3$ and $R_6$ are the same and are selected from $C_1$-$C_{17}$ alkyl, $C_2$-$C_{17}$ alkenyl or

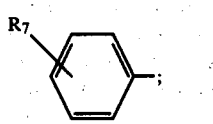

$R_4$ and $R_5$ are methyl; $R_7$ is hydrogen, halogen or $C_1$-$C_4$ alkyl; m is 1.

15. The method according to claim 12, wherein the insects are Lepidopterous insects, and the compound is applied at the rate of from 0.14 kg/hectare to 11.2 kg/hectare.

16. The method according to claim 12, wherein the insects are ants, Family Formicidae, and the compound is applied at the rate of from 2.5 g/hectare to 37.5 g/hectare.

17. The method according to claim 12, wherein the insects are termites, cockroaches, grasshoppers, flies and ants, Family Formicidae, and the compound is applied incorporated in a bait at a concentration of from 0.125% to 2.0% by weight.

18. The method according to claim 16, wherein the ants are the southern fire ant *Solenopsis xyloni*, the black imported fire ant *Solenopsis richteri* and the red imported fire ant *Solenopsis invicta*.

19. The method according to claim 12, wherein the compound is 1,5-bis($\alpha,\alpha,\alpha$-trifluoro-p-tolyl)-1,4-pentadien-3-one(1-acetyl-1,4,5,6-tetrahydro-5,5-dimethyl-2-pyrimidinyl)hydrazone.

20. The method according to claim 12, wherein the compound is 1,5-bis($\alpha,\alpha,\alpha$-trifluoro-p-tolyl)-1,4-pentadien-3-one(1,4,5,6-tetrahydro-1-isobutyryl-5,5-dimethyl-2-pyrimidinyl)hydrazone.

21. The method according to claim 12, wherein the compound is 1,5-bis($\alpha,\alpha,\alpha$-trifluoro-p-tolyl)-1,4-pentadien-3-one(1-benzoyl-1,4,5,6-tetrahydro-5,5-dimethyl-2-pyrimidinyl)hydrazone.

22. A method for protecting agronomic crops, trees, shrubs and ornamentals from attack by insects comprising applying to said crops an insecticidally effective amount of a compound represented by formula:

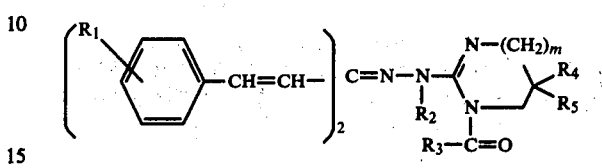

wherein $R_1$ is in the meta or para position and is selected from the group consisting of halogen, $CF_3-$, $CHF_2CF_2O-$ or $CH_nF_{3-n}Y-$; $R_2$ is hydrogen or

$R_3$ and $R_6$ may be the same or different and are selected from $C_1$-$C_{17}$ alkyl, $C_2$-$C_{17}$ alkenyl or

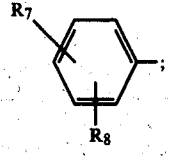

$R_4$ and $R_5$ are each hydrogen or methyl; $R_7$ and $R_8$ are hydrogen, halogen, $C_1$-$C_4$ alkyl or $C_1$-$C_4$ alkoxy; Y is oxygen or sulfur; m is an integer selected from 0, 1 or 2; n is an integer selected from 0 or 1.

23. The method according to claim 22, wherein said insects are Lepidopterous insects, and said compound is applied at the rate of from 0.28 kg/hectare to 11.2 kg/hectare.

24. The method according to claim 22, wherein said insects are ants, Family Formicidae, and said compound is applied at the rate of from 2.5 g/hectare to 37.5 g/hectare.

25. The method according to claim 22, wherein the insects are termites, cockroaches, grasshoppers, flies and ants, Family Formicidae, and the compound is applied incorporated in a bait at a concentration of from 0.125% to 2.0% by weight.

26. The method according to claim 24, wherein the ants are the southern fire ant *Solenopsis xyloni*, the black imported fire ant *Solenopsis richteri* and the red imported fire ant *Solenopsis invicta*.

* * * * *